US011599319B2

(12) United States Patent
Nomura

(10) Patent No.: US 11,599,319 B2
(45) Date of Patent: Mar. 7, 2023

(54) DISPLAY APPARATUS, DISPLAY SYSTEM, AND STORAGE MEDIUM

(71) Applicant: KONICA MINOLTA, INC., Tokyo (JP)

(72) Inventor: Seiji Nomura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 34 days.

(21) Appl. No.: 16/934,120

(22) Filed: Jul. 21, 2020

(65) Prior Publication Data

US 2021/0064319 A1 Mar. 4, 2021

(30) Foreign Application Priority Data

Aug. 29, 2019 (JP) .............................. JP2019-156497

(51) Int. Cl.
*G06F 3/14* (2006.01)
*G16H 10/60* (2018.01)

(52) U.S. Cl.
CPC .............. *G06F 3/14* (2013.01); *G16H 10/60* (2018.01)

(58) Field of Classification Search
CPC .................................. G06F 3/14; G16H 10/60
See application file for complete search history.

(56) References Cited

U.S. PATENT DOCUMENTS

2008/0306766 A1* 12/2008 Ozeki ................... G06Q 10/06
                                                            705/2
2019/0108918 A1* 4/2019 Akashi .................. G06Q 40/08

FOREIGN PATENT DOCUMENTS

| JP | 2001265311 A | 9/2001 |
|----|--------------|--------|
| JP | 2005025669 A | 1/2005 |
| JP | 2015228103 A | 12/2015 |

OTHER PUBLICATIONS

Japanese Office Action (and English language translation thereof) dated Jan. 17, 2023, issued in counterpart Japanese Application No. 2019-156497.

* cited by examiner

*Primary Examiner* — Xin Sheng
(74) *Attorney, Agent, or Firm* — Holtz, Holtz & Volek PC

(57) ABSTRACT

A display apparatus includes a display and a hardware processor. The display displays timeline screens showing different kinds of display target information in chronological order. The hardware processor performs control to synchronize displayed periods of the timeline screens so that the timeline screens show the display target information of an identical period.

11 Claims, 7 Drawing Sheets

DISPLAY APPARATUS, DISPLAY SYSTEM, AND STORAGE MEDIUM

CROSS-REFERENCE TO RELATED APPLICATIONS

The entire disclosure of Japanese Patent Application No. 2019-156497 filed on Aug. 29, 2019 is incorporated herein by reference in its entirety.

BACKGROUND

Technological Field

The present disclosure relates to a display apparatus, a display system, and a storage medium.

Description of Related Art

In the medical field, various technologies are available for showing medical information of a patient to be easily viewed.

For example, according to JP 2005-25669A, medical report data on interpretation of medical image data is associated with a diagnosis target region in the medical image data and stored in a database server. In displaying the report data, the medical image data is also displayed so as to specify the diagnosis target region.

There is also used a timeline display that shows a list of multiple pieces of medical information on a patient, such as image information and examination information, along a time axis.

SUMMARY

In a case where multiple systems of departments in a medical facility provide their respective timeline screens, or in a case where multiple medical facilities cooperating with each other provide their respective timeline screens, multiple timeline screens exist for one patient. For example, FIG. 3 exemplifies a first timeline screen 351 provided by the system of an image examination department. The first timeline screen 351 provides timeline display of medical images obtained in various image examinations. FIG. 4 exemplifies a second timeline screen 352 provided by the system of another department (e.g., laboratory examination department). The second timeline screen 352 provides timeline display of multiple pieces of information other than medical images, such as examination result information and medication history. When multiple timeline screens exist for one patient as described above, the timeline screens show different displayed periods. A user has to make the displayed periods uniform by manipulating the individual timeline screens and changing their respective displayed periods. This takes time and effort.

In a case where multiple timeline screens show information other than medical information as display target information, the user also has to make the displayed periods uniform by manipulating the individual timeline screens and changing their respective displayed periods. This takes time and effort.

Objects of the present invention include, in displaying multiple timeline screens, saving time and effort of manipulating the individual timeline screens and changing their respective displayed periods to make the displayed periods uniform.

To achieve at least one of the abovementioned objects, according to an aspect of the present invention, there is provided a display apparatus including: a display that displays timeline screens showing different kinds of display target information in chronological order; and a hardware processor that performs control to synchronize displayed periods of the timeline screens so that the timeline screens show the display target information of an identical period.

To achieve at least one of the abovementioned objects, according to another aspect of the present invention, there is provided a display system, including:

a display apparatus; and servers that cause the display apparatus to display respective timeline screens showing different kinds of display target information in chronological order, the display apparatus and the servers being connected to each other for communication, wherein in response to a displayed period of a timeline screen that is among the timeline screens and displayed on the display apparatus by a server among the servers being changed, the server obtains information on the changed displayed period and sends the obtained information to an other server among the servers, and in response to receiving the information on the displayed period from the server, a server among the other server causes a timeline screen that is among the timeline screens and displayed on the display apparatus by the server among the other server to show the display target information of the displayed period indicated by the received information.

To achieve at least one of the abovementioned objects, according to another aspect of the present invention, there is provided a display system, including:

a display apparatus; and servers that cause the display apparatus to display respective timeline screens showing different kinds of display target information in chronological order, the display apparatus and the servers being connected to each other for communication, wherein in response to a displayed period of a timeline screen that is among the timeline screens and displayed on the display apparatus by a server among the servers being changed, the server obtains information on the changed displayed period and sends the obtained information to the display apparatus, and in response to receiving the information on the displayed period from the server, the display apparatus sends the received information to an other server among the servers that corresponds to an other timeline screen among the timeline screens, the other timeline screen being displayed on the display apparatus and different from the timeline screen showing the displayed period, and in response to receiving the information on the displayed period from the display apparatus, a server among the other server causes a timeline screen among the other timeline screen being displayed on the display apparatus by the server among the other server to show the display target information of the displayed period indicated by the received information.

To achieve at least one of the abovementioned objects, according to another aspect of the present invention, there is provided a display system, including:

a display apparatus that generates and displays a first timeline screen showing first display target information in chronological order; and a server that causes the display apparatus to display a second timeline screen showing second display target information in chronological order, a kind of the second display target information being different from a kind of the first display target information, the display apparatus and the server being connected to each other for communication, wherein in response to a displayed period of the first timeline screen being changed, the display apparatus obtains information on the changed displayed period and sends the obtained information to the server, and in response to receiving the information on the displayed period from the display apparatus, the server causes the second timeline screen to show the second display target information of the displayed period indicated by the received information.

To achieve at least one of the abovementioned objects, according to another aspect of the present invention, there is provided a non-transitory computer-readable storage medium storing a program that causes a computer to perform:

displaying timeline screens showing different kinds of display target information in chronological order; and performing control to synchronize displayed periods of the timeline screens so that the timeline screens show the display target information of an identical period.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION OF THE EMBODIMENTS

Figure 1:
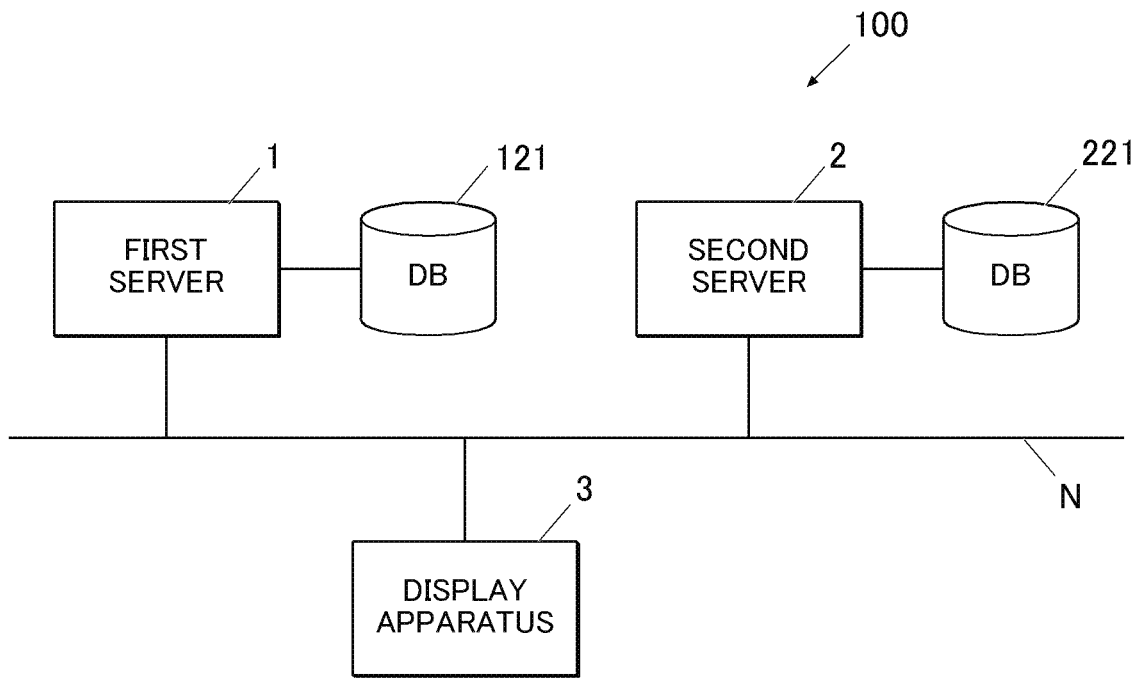
FIG. 1 is an overall configuration of a display system according to embodiments of the present invention.

Hereinafter, one or more embodiments of the present invention will be described with reference to the drawings. However, the scope of the invention is not limited to the disclosed embodiments.

In the present disclosure, display target information is information to be displayed in chronological order on timeline screens including a first timeline screen 351 and a second timeline screen 352.

Examples of the display target information include medical information and nursing-care information of an identical patient. The medical information is generated on the patient's conditions and so forth that are obtained through medical treatment. The nursing-care information relates to nursing care.

Examples of the medical information include examination information, examination facility information, examination department information, medical images, examination result information, medical records, and medication histories.

The examination information relates to an examination(s). Examples of the examination information include examination ID, examination date, modalities (e.g., computed tomography (CT), digital radiography (DR), computed radiography (CR), ultrasonography (US), magnetic resonance imaging (MRI)), examined region, and purpose of examination. The examination facility information relates to an examination facility(ies). Examples of the examination facility information include the name and location of an examination facility. The examination department information relates to an examination department(s). Examples of the examination department information include the name and location of an examination department. Medical images are the results of imaging or measuring a human body for medical service or medical science, the results being in the form of images. Examples of medical images include X-ray images, MRI images, and CT images, and may be icon images thereof. The examination result information relates to results of examinations. Examples of the examination result information include information on results of blood tests and urine tests.

Examples of different kinds of display target information include different kinds of medical information, such as examination information, examination facility information, examination department information, medical images, examination result information, medical records, and medication histories. Examples of different kinds of display target information also include different kinds of medical image information, such as X-ray images, MRI images, CT images, and icon images thereof.

That is, different kinds of display target information may be different kinds of medical information/nursing-care information or different kinds of information categorized as the same kind of medical information/nursing-care information. Different kinds of display target information may be obtained from different medical facilities, different departments in the same medical facility, or different medical systems.

First Embodiment

[Configuration of Display System 100]

First, a configuration of a first embodiment is described.

FIG. 1 shows an overall configuration of a display system 100 in this embodiment.

As shown in FIG. 1, the display system 100 includes: a first server 1 including a data base (DB) 121; a second server 2 including a DB 221; and a display apparatus 3 that are connected to each other through a communication network N, such as a local area network (LAN). The components consisting the display system 100 conform to the Health Level Seven (HL7) standard and/or the Digital Image and Communications in Medicine (DICOM) standard, and communicate with each other in accordance with HL7 and/or DICOM.

The DB 121 and the DB 221 are databases storing different kinds of medical information. The medical information is generated on a patient's conditions and so forth obtained through medical treatment. Examples of the medical information include medical images, examination result information such as results of laboratory tests, medical records, and medication history. In the embodiments described below, the DB 121 stores medical images, and the DB 221 stores examination result information as an example. However, the present invention is not limited to this.

[Configuration of First Server 1]

The first server 1 is a server of a system for an image examination department, such as Picture Archiving and Communication Systems (PACS). The first server 1 includes the DB 121 storing medical images obtained in the medical facility and manages the medical images.

Figure 2:
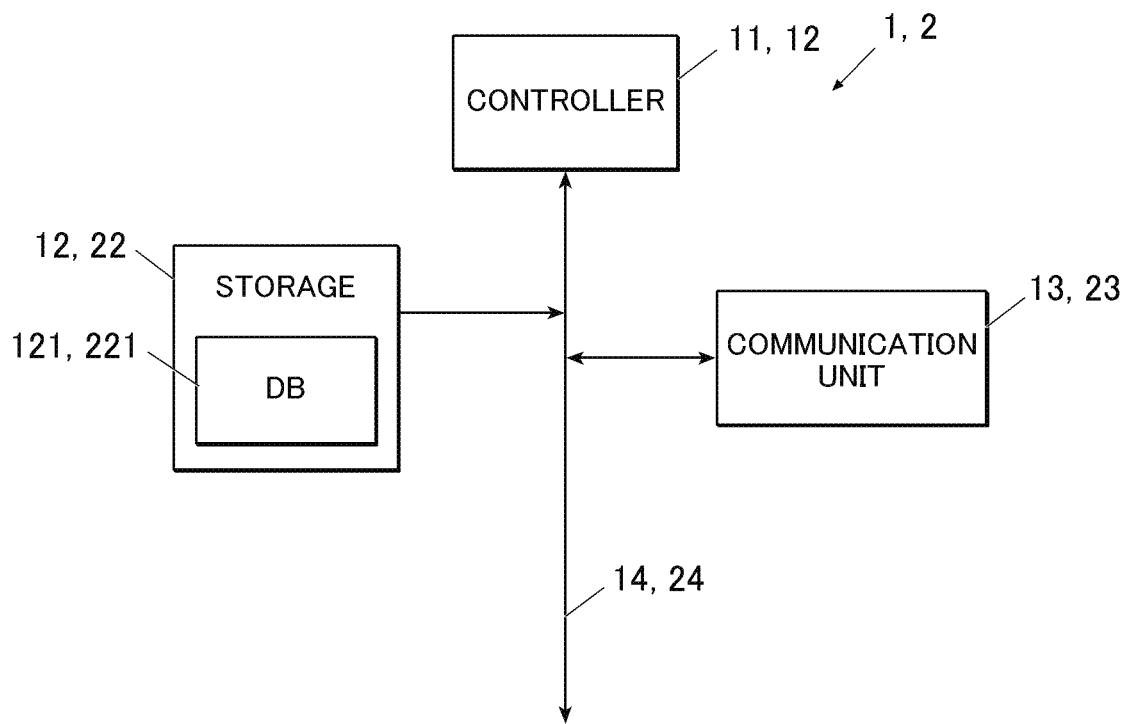
FIG. 2 is a block diagram showing a functional configuration of a first server and a second server in FIG. 1.

FIG. 2 shows a functional configuration of the first server 1. As shown in FIG. 2, the first server 1 includes a controller 11, a storage 12, and a communication unit 13 that are connected to each other through a bus 14.

The controller 11 includes a CPU, a ROM, and a RAM, and integrally controls processing operations of the components of the first server 1. More specifically, the CPU reads various processing programs stored in the ROM, loads the read programs into the RAM, and performs various processes in cooperation with the programs.

For example, in this embodiment, the ROM of the controller 11 stores various programs, such as a program for causing the first server 1 to function as a Web (World Wide Web) server that communicates with a Web browser(s) in accordance with HTTP protocols and provides the Web browser with various Web screens. The CPU of the controller 11 performs the following processes in accordance with the programs.

Figure 3:
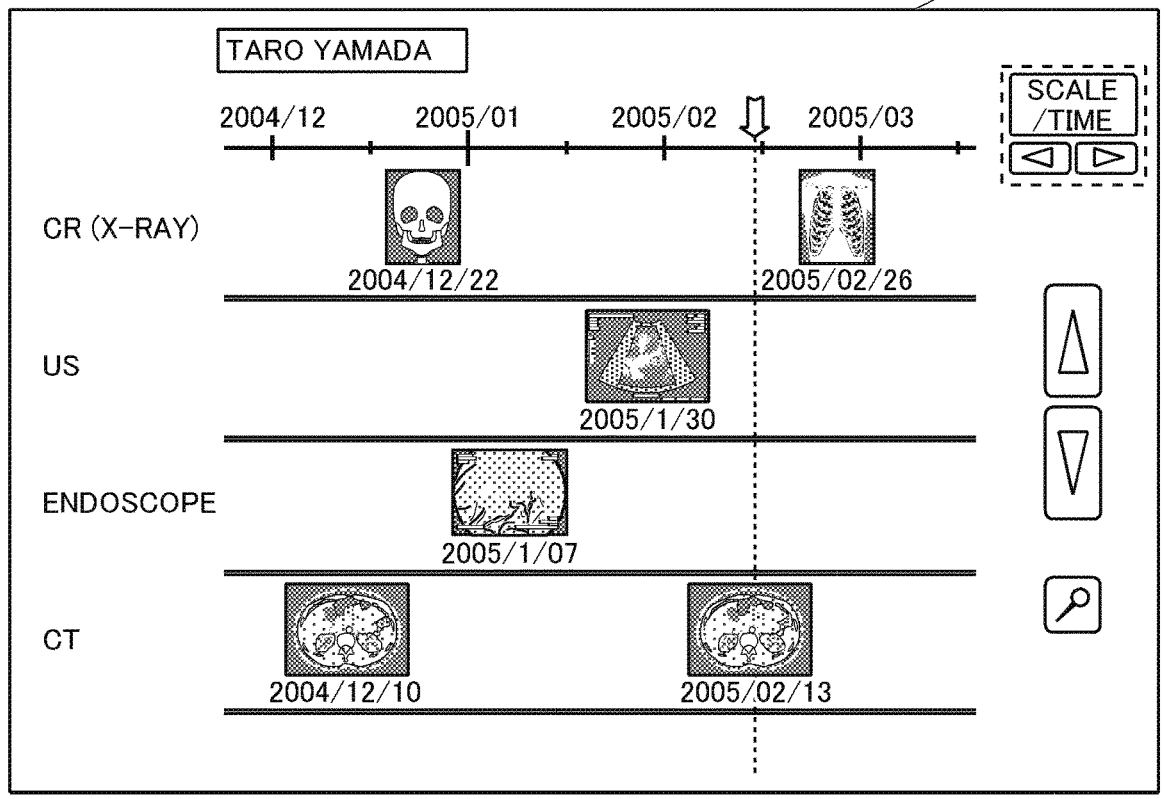
FIG. 3 shows an example of a first timeline screen.

For example, when instructed to perform timeline display of a patient by the Web browser of the display apparatus 3, the controller 11 reads out medical images of the patient from the DB 121; generates a first timeline screen 351 (Web screen, see FIG. 3) on which the medical images are chronologically arranged and shown; sends the first timeline screen 351 to the display apparatus 3 through the communication unit 13; and causes The Web browser of the display apparatus 3 to display the first timeline screen 351.

For example, when receiving, from the Web browser of the display apparatus 3, information on operations (operation information) performed on the first timeline screen 351 displayed on the display apparatus 3, the controller 11 determines whether a displayed period of the first timeline screen 351 is changed on the basis of the received operation information. When determining that the displayed period is changed, the controller 11 obtains displayed period information of the first timeline screen 351 and sends the information to the second server 2. Herein, the displayed period of the first timeline screen 351 is a period of timeline that is shown on the first timeline screen 351. The displayed period information of the first timeline screen 351 is information on the displayed period of the first timeline screen 351 (information indicating the displayed period). The displayed period information includes date information on at least the start and end dates of the displayed period.

For example, when receiving displayed period information of a second timeline screen 352 from a server (herein, the second server 2) different from the first server 1 in the display system 100, the controller 11 determines whether the first timeline screen 351 is displayed on the display apparatus 3. When determining that the first timeline screen 351 is displayed, the controller 11 generates the first timeline screen 351 the displayed period of which is changed to be the displayed period indicated by the display period information of the second server 2, and causes the Web browser of the display apparatus 3 to display the changed first timeline screen 351.

The storage 12 includes a hard disk and/or a nonvolatile semiconductor memory and stores various kinds of data. The storage 12 has the DB 121. The DB 121 stores medical images that are obtained in the medical facility and associated with patient information (e.g., ID, name, birthdate, age, sex, height, and weight of a patient) and/or examination information (e.g., ID and date of examination, modalities such as CT, CR, US, and MRI, examined region, and purpose of examination).

The communication unit 13 includes a network interface and exchanges data with external apparatuses connected through the communication network N.

[Configuration of Second Server 2]

The second server 2 is, for example, a server of a system for an examination department different from the image examination department. The second server 2 has the DB 221 that stores examination result information on blood and urine tests, for example, and manages the examination result information.

FIG. 2 shows a functional configuration of the second server 2. As shown in FIG. 2, the second server 2 includes a controller 21, a storage 22, and a communication unit 23 that are connected to each other through a bus 24.

The controller 21 includes a CPU, a ROM, and a RAM, and integrally controls processing operations of the components of the second server 2. More specifically, the CPU reads various processing programs stored in the ROM, loads the read programs into the RAM, and performs various processes in cooperation with the programs.

For example, in this embodiment, the ROM of the controller 21 stores various programs, such as a program for causing the second server 2 to function as a Web server that communicates with a Web browser(s) in accordance with HTTP protocols and provides the Web browser with various Web screens. The CPU of the controller 21 performs the following processes in accordance with the various programs.

Figure 4:
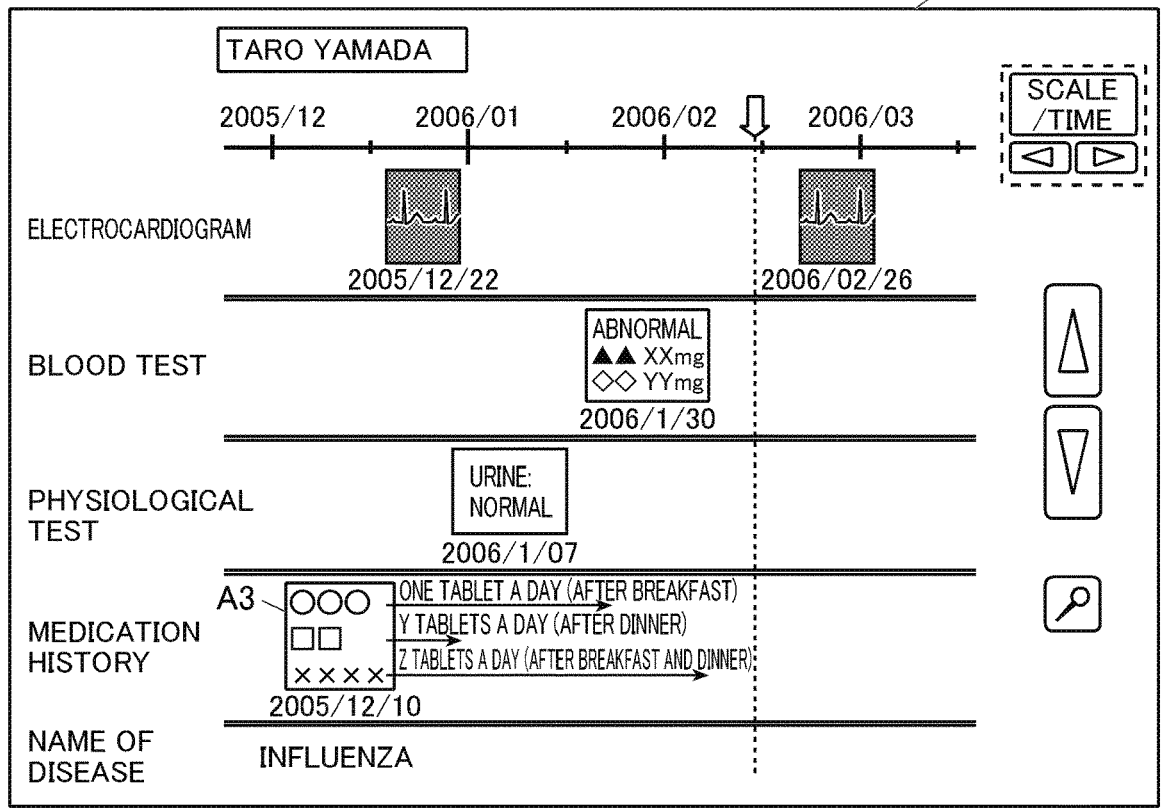
FIG. 4 shows an example of a second timeline screen.

For example, when instructed to perform timeline display of a patient by the Web browser of the display apparatus 3, the controller 21 reads out examination result information of the patient from the DB 221; generates a second timeline screen 352 (Web screen, see FIG. 4) on which the examination result information is chronologically arranged and shown; sends the second timeline screen 352 to the display apparatus 3 through the communication unit 23; and causes the Web browser of the display apparatus 3 to display the second timeline screen 352.

For example, when receiving information on operations (operation information) performed on the second timeline screen 352 displayed on the display apparatus 3 from the Web browser, the controller 21 determines whether a displayed period of the second timeline screen 352 is changed on the basis of the received operation information. When determining that the displayed period is changed, the controller 21 obtains displayed period information of the second timeline screen 352 and sends the information to the first server 1. Herein, the displayed period of the second timeline screen 352 is a period of timeline that is shown on the second timeline screen 352. The displayed period information of the second timeline screen 352 is information on the displayed period of the second timeline screen 352 (information indicating the displayed period). The displayed period information includes date information on at least the start and end dates of the displayed period.

For example, when receiving display period information of the first timeline screen 351 from a server different from the second server 2 in the display system 100 (herein, the first server 1), the controller 21 determines whether the second timeline screen 352 is displayed on the display apparatus 3. When determining that the second timeline screen 352 is displayed, the controller 21 generates the second timeline screen 352 the displayed period of which is changed to be the displayed period indicated by the display period information of the first server 1, and causes the Web browser of the display apparatus 3 to display the changed second timeline screen 352.

The storage 22 includes a hard disk and/or a nonvolatile semiconductor memory and stores various kinds of data. The storage 22 has the DB 221. The DB 221 stores results of examinations different from image examinations (e.g., blood and urine tests) of a patient in the medical facility and associated with patient information (e.g., ID, name, birthdate, age, sex, height, and weight of the patient) and/or examination information (e.g., ID and date of examination, and examination items).

The communication unit 23 includes a network interface and exchanges data with external apparatuses connected through the communication network N.

[Configuration of Display Apparatus 3]

The display apparatus 3 has a Web browser and can display Web screens provided by the first server 1 and the second server 2.

Figure 5:
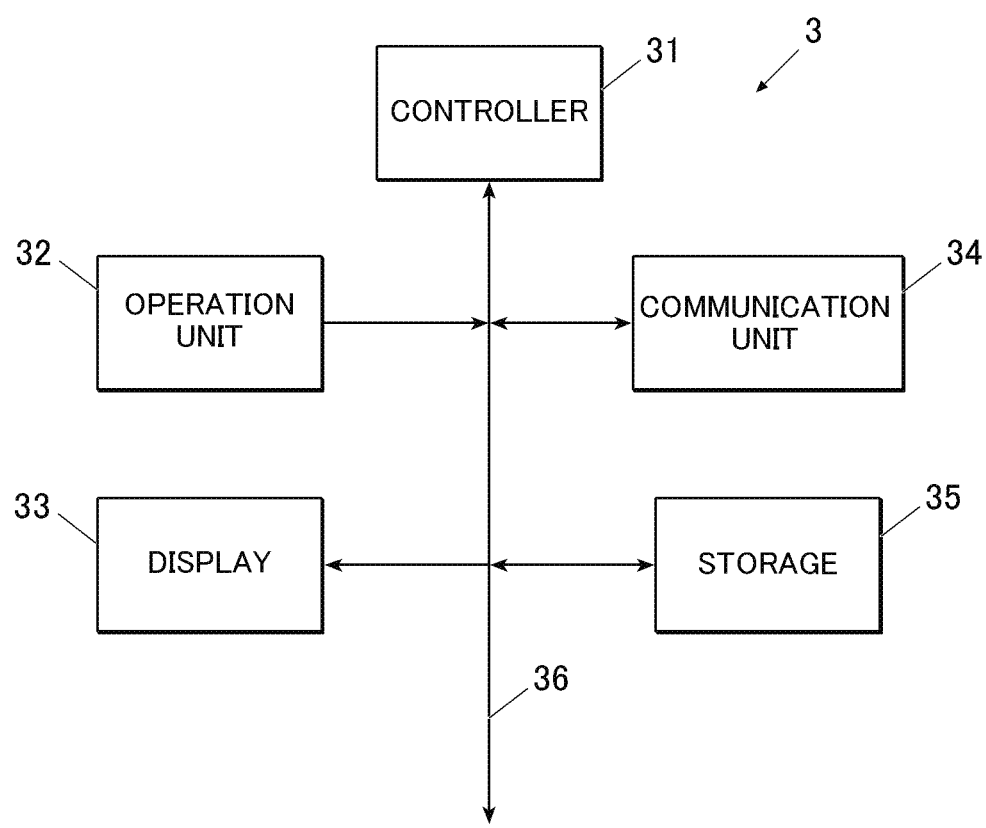
FIG. 5 is a block diagram showing a functional configuration of a display apparatus in FIG. 1.

FIG. 5 shows a functional configuration of the display apparatus 3. As shown in FIG. 5, the display apparatus 3 includes a controller 31 (hardware processor), an operation unit 32, a display 33, a communication unit 34, and a storage 35 that are connected to each other through a bus 36.

The controller 31 includes a CPU, a ROM, and a RAM, and integrally controls processing operations of the components of the display apparatus 3. More specifically, the CPU reads various processing programs stored in the ROM, loads the read programs into the RAM, and performs various processes in cooperation with the programs.

For example, the controller 31 causes the Web browser stored in the ROM to display Web screens including the first timeline screen 351 provided by the first server 1 and the second timeline screen 352 provided by the second server 2. The controller 31 also obtains, with the Web browser, operation information on a Web screen and sends, through the communication unit 34, the operation information to a Web server corresponding to the Web screen.

The operation unit 32 includes a keyboard including cursor keys, character and number entry keys, and various function keys and a pointing device such as a mouse. The operation unit 32 outputs, to the controller 31, operation signals input by key operations on the keyboard or by mouse operations. When the operation unit 32 includes a touchscreen superposed on the display 33, the operation unit 32 outputs, to the controller 31, operation signals corresponding to the positions of touching operations with a user's finger or the like.

The display 33 includes a monitor, such as a liquid crystal display (LCD), and displays various screens in accordance with instructions of display signals input by the controller 31. The display 33 may have one or more monitors.

The communication unit 34 includes a network interface and exchanges data with external apparatuses connected through the communication network N.

The storage 35 includes a hard disk and/or a nonvolatile semiconductor memory and stores various kinds of data.

[Operations of Display System 100]

Next, operations of the display system 100 are described.

Figure 6:
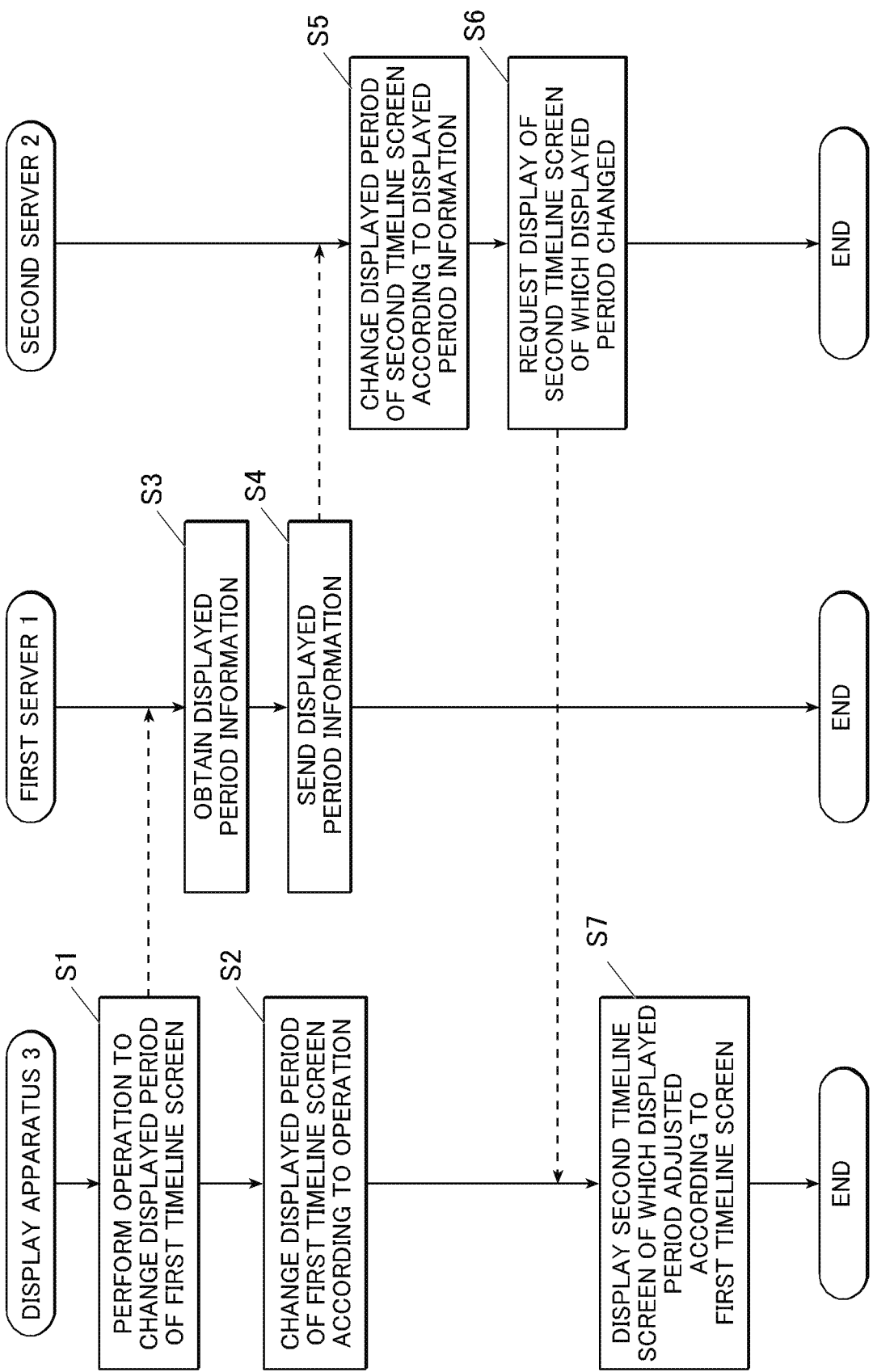
FIG. 6 shows procedure of a displayed period synchronization sequence performed by the display system in a first embodiment.

FIG. 6 is a flowchart showing procedure of a displayed period synchronization sequence performed by the components of the display system 100. In FIG. 6, the steps by the display apparatus 3 are performed by the controller 31 of the display apparatus 3; the steps by the first server 1 are performed by the controller 11 of the first server 1; and the steps by the second server 2 are performed by the controller 21 of the second server 2.

Herein, the display apparatus 3 is displaying (i) the first timeline screen 351 as one timeline screen chronologically showing a kind of display target information of a patient (herein, image information) and (ii) the second timeline screen 352 as the other timeline screen chronologically showing a different kind of display target information of the same patient (herein, examination result information). Display target information is information to be displayed chronologically on timeline screens including the first timeline screen 351 and the second timeline screen 352.

When the display apparatus 3 receives an operation (e.g., scrolling) performed with the operation unit 32 to change the displayed period of the first timeline screen 351, the controller 31 obtains the operation information through the Web browser. The controller 31 then sends the operation information to the first server 1 through the communication unit 34 (STEP S1). The controller 31 also changes the displayed period of the first timeline screen 351 according to the operation, and causes the display 33 to display the changed first timeline screen 351 (STEP S2). STEP S2 may be performed in cooperation with the first server 1.

When receiving, through the communication unit 13, the operation information on the operation performed on the first timeline screen 351 from the display apparatus 3, the controller 11 of the first server 1 determines on the basis of the operation information whether the displayed period of the first timeline screen 351 is changed. When determining that the displayed period is changed, the controller 11 obtains displayed period information of the first timeline screen 351 (STEP S3). The controller 10 then sends the obtained displayed period information to the second server 2 through the communication unit 13 (STEP S4).

When receiving, through the communication unit 23, the displayed period information from the first server 1, the controller 21 of the second server 2 generates, on the basis of the received displayed period information, the second timeline screen 352 the displayed period of which is changed according to the first timeline screen 351 (the second timeline screen 252 showing the examination result information of the displayed period indicated by the displayed period information) (STEP S5). The controller 21 then requests the Web browser of the display apparatus 3 to display the second timeline screen 352 the displayed period of which is changed (STEP S6).

When receiving the request to display the second timeline screen 352 the displayed period of which is changed from the second server 2, the controller 31 of the display apparatus 3 causes the Web browser to display, on the display 33, the second timeline screen 352 the displayed period of which is changed according to the first timeline screen 351 (STEP S7). Then the displayed period synchronization sequence ends.

According to the first embodiment, displayed periods of multiple timeline screens being displayed on the display apparatus 3 can be made uniform. This can save time and effort of manipulating individual timeline screens and changing their respective displayed periods to make these displayed periods uniform.

Timeline screens are in most cases Web screens displayed on a Web browser(s). It has been difficult to make displayed periods of multiple timeline screens uniform owing to difficulty in communication between individual Web screens. According to the first embodiment, when a displayed period of a timeline screen is changed, a Web server displaying the timeline screen obtains displayed period information of the timeline screen and sends the information to another Web server displaying another timeline screen. The displayed period of another timeline screen can be changed according to the changed displayed period of the Web server. That is, the displayed periods of multiple timeline screens can be synchronized.

Further, according to the first embodiment, the displayed periods of timeline screens for multiple systems can be made uniform, so that information stored in the multiple systems can be viewed cross-sectionally. For example, medical information of a patient stored in multiple department systems in a medical facility can be viewed cross-sectionally.

FIG. 6 shows a case of changing the displayed period of the first timeline screen 351 and adjusting the displayed period of the second timeline screen 352 to the displayed period of the first timeline screen 351. In a case of changing the displayed period of the second timeline screen 352 and adjusting the displayed period of the first timeline screen 351 to the displayed period of the second timeline screen 352, the display system 100 performs a sequence in which (i) the first server 1 and the second server 2 are exchanged and (ii) the first timeline screen 351 and the second timeline screen 352 are exchanged in FIG. 6.

Further, in the above-described first embodiment, the display apparatus 3 is displaying two timeline screens as an example. However, the number of timeline screens being displayed may be three or more. In a case where three or more timeline screens are displayed, and the displayed period of one timeline screen displayed on the display apparatus 3 is changed, a server corresponding to the timeline screen obtains displayed period information of the changed timeline screen and sends the information to the other servers. In response to receiving displayed period information from any of the other servers, the server causes the display apparatus 3 to display, on the timeline screen being displayed on the display apparatus 3 by the server, display target information (e.g., medical information such as examination information, examination facility information, examination department information, medical images, and examination result information) of the displayed period indicated by the received displayed period information. Thus, displayed periods of multiple timeline screens can be made uniform.

Further, in the above-described first embodiment, when the displayed period of one timeline screen is changed, a server among the multiple servers corresponding to the one timeline screen obtains information on the changed displayed period and sends the information to the other servers. Alternatively, the obtained displayed period information may be sent to the display apparatus 3. The display apparatus 3 may then send the displayed period information to the other servers corresponding to the other timeline screens. In response to receiving the displayed period information from the display apparatus 3, the other servers may then cause the display apparatus 3 to display, on their corresponding timeline screens displayed on the displayed apparatus 3, display target information of the displayed period indicated by the displayed period information.

Second Embodiment

Hereinafter, a second embodiment of the present invention is described.

The second embodiment exemplifies a case where one of the first timeline screen and the second timeline screen is a Web screen, and the other is a screen displayed by a program (application) stored in the display apparatus 3. In the embodiment, the first timeline screen is a screen displayed by the application, and the second timeline screen is a Web screen. However, the first and second timeline screens may be replaced with each other.

[Configuration in Second Embodiment]

The configuration of the system in the second embodiment is the same as the display system 100 shown in FIG. 1 described in the first embodiment. The configurations of the first server 1, the second server 2, and the display apparatus 3, which consist the display system 100, are also the same as the configurations shown in FIG. 2 and FIG. 5.

In the second embodiment, the ROM of the controller 31 of the display apparatus 3 stores an application for: reading out medical images of a patient specified with the operation unit 32 from the DB 121 of the first server 1; generating the first timeline screen 353 (see FIG. 3) on which the medical images are arranged chronologically; causing the display 33 to display the first timeline screen 353; outputting operation information on operations performed by a user on the first timeline screen 353; and changing the contents displayed on the first timeline screen 353 according to the user's operation.

Further, the ROM of the controller 31 also stores a program for: obtaining the operation information output by the application; determining, on the basis of the obtained operation information, whether any operation is performed to change the displayed period of the first timeline screen 353; when determining that an operation to change the displayed period is performed, obtaining displayed period information of the first timeline screen 353; sending the displayed period information to the second server 2 through the communication unit 34; and, when receiving displayed period information of the second timeline screen 352 from the second server 2, causing the application to change the displayed period of the first timeline screen 353 to be the displayed period indicated by the received displayed period information and display the changed first timeline screen 353 on the display 33. Herein, the displayed period of the first timeline screen 353 is a period of timeline that is shown on the first timeline screen 353. The displayed period information of the first timeline screen 353 is information on the displayed period of the first timeline screen 353 (information indicating the displayed period). The displayed period information includes date information on at least the start and end dates of the displayed period.

The ROM of the controller 31 of the display apparatus 3 also stores a Web browser.

Further, the ROM of the controller 11 of the first server 1 stores a program for reading out medical images requested by the display apparatus 3 from the DB 121 and sending the images to the display apparatus 3 through the communication unit 13.

Further, the ROM of the controller 21 of the second server 2 stores, as with the first embodiment, a web server program for causing the second server 2 to function as a Web server. In accordance with the Web server program, the CPU of the controller 21 provides the Web browser with various Web screens. For example, when instructed to perform timeline display for a patient by the Web browser of the display apparatus 3, the controller 21 reads out examination result information of the patient from the DB 221, generates the second timeline screen 352 (Web screen) on which the examination result information is chronologically arranged, and causes the Web browser of the display apparatus 3 to display the second timeline screen 352.

The ROM of the controller 21 of the second server 2 also stores a program for: determining, when receiving operation information of the second timeline screen 352 from the Web browser, whether the displayed period of the second timeline screen 352 is changed on the basis of the received operation information; and, when determining that the displayed period is changed, sending displayed period information of the second timeline screen 352 to the display apparatus 3.

The ROM of the controller 21 of the second server 2 also stores a program for: determining, when receiving displayed period information of the first timeline screen 353 from the display apparatus 3 through the communication 23, whether the second timeline screen 352 is displayed on the Web browser of the display apparatus 3; when determining that the second timeline screen 352 is displayed, generating the second timeline screen 352 that is adjusted to show the displayed period indicated by the received displayed period information; and causing the Web browser of the display apparatus 3 to display the changed second timeline screen 352.

[Operations of Second Embodiment]

Next, operations of the second embodiment are described.

Figure 7:
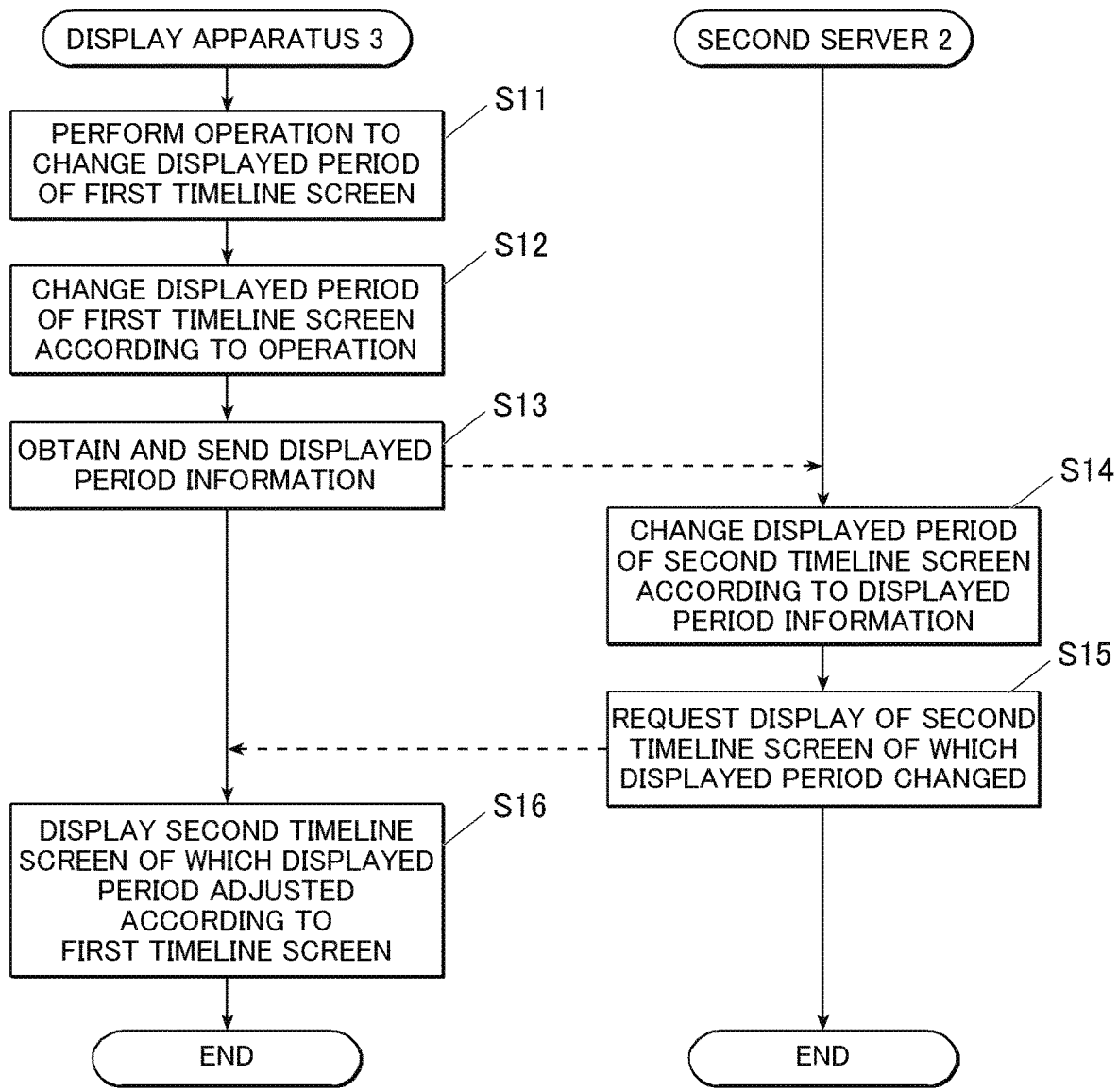
FIG. 7 shows procedure of a first displayed period synchronization sequence performed by the display system in a second embodiment.

FIG. 7 is a flowchart showing procedure of a first displayed period synchronization sequence performed by the components of the display system 100 in the second embodiment. In the first displayed period synchronization sequence, the displayed period of the second timeline screen 352 as a web screen is adjusted to the displayed period of the first timeline screen 353, when an operation to change the displayed period of the first timeline screen 353 is performed on the display apparatus 3.

In FIG. 7, the steps by the display apparatus 3 are performed by the controller 31 of the display apparatus 3, and the steps by the second server 2 are performed by the controller 21 of the second server 2.

Herein, the display apparatus 3 is displaying the first timeline screen 353 and the second timeline screen 352 of a patient (display target patient).

When the display apparatus 3 receives an operation performed with the operation unit 32 to change the displayed period of the first timeline screen 353 (STEP S11), the controller 31 changes the displayed period of the first timeline screen 353 according to the operation, and causes the display 33 to display the changed first timeline screen 353 (STEP S12).

For example, the controller 31 changes the displayed period of the first timeline screen 353 by: obtaining, from the DB 121, medical images of the display target patient that have been taken during the displayed period; generating the first timeline screen 353 on which the obtained medical images are arranged chronologically; and displaying the first timeline screen 353 on the display 33.

On the basis of the operation information on the performed operation, the controller 31 obtains displayed period information and sends thereof to the second server 2 through the communication unit 34 (STEP S13).

When receiving the displayed period information of the first timeline screen 353 from the display apparatus 3 through the communication unit 23, the controller 21 of the second server 2 generates, on the basis of the received displayed period information, the second timeline screen 352 the displayed period of which is changed according to the first timeline screen 353 (the second timeline screen 252 showing the examination result information of the displayed period indicated by the displayed period information) (STEP S14). The controller 21 then requests the Web browser of the display apparatus 3 to display the second timeline screen 352 the displayed period of which is changed (STEP S15).

When receiving the request to display the second timeline screen 352 the displayed period of which is changed from the second server 2, the controller 31 of the display apparatus 3 causes the Web browser to display, on the display 33, the second timeline screen 352 the displayed period of which is adjusted according to the first timeline screen 353 (STEP S16). Then the first displayed period synchronization sequence ends.

Figure 8:
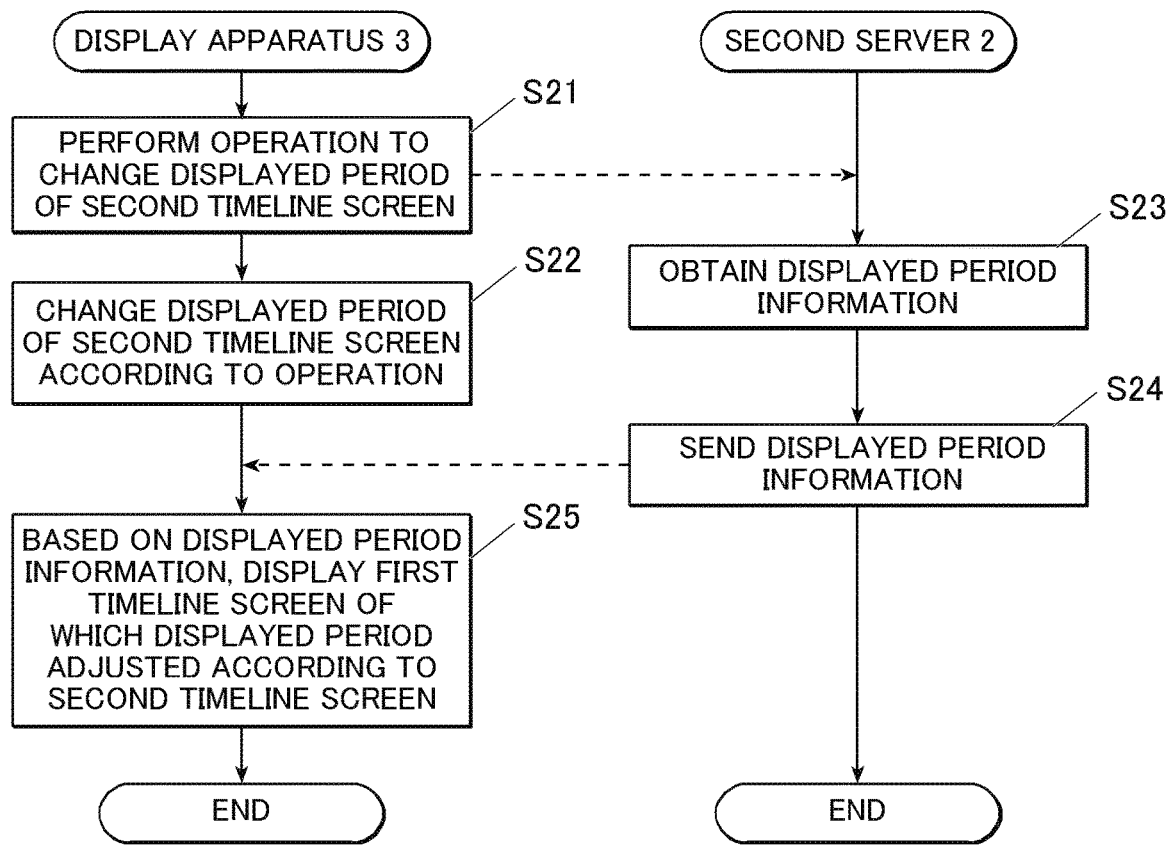
FIG. 8 shows procedure of a second displayed period synchronization sequence performed by the display system in the second embodiment.

FIG. 8 is a flowchart showing procedure of a second displayed period synchronization sequence performed by the components of the display system 100 in the second embodiment. In the second displayed period synchronization sequence, the displayed period of the first timeline screen 353 is adjusted to the displayed period of the second timeline screen 352 as a Web screen, when an operation to change the displayed period of the second timeline screen 352 is performed on the display apparatus 3.

In FIG. 8, the steps by the display apparatus 3 are performed by the controller 31 of the display apparatus 3, and the steps by the second server 2 are performed by the controller 21 of the second server 2.

Herein, the display apparatus 3 is displaying the first timeline screen 353 and the second timeline screen 352 of a patient (display target patient).

When the display apparatus 3 receives an operation performed with the operation unit 32 to change the displayed period of the second timeline screen 352, the controller 31 obtains the operation information through the Web browser. The controller 31 then sends the obtained operation information to the second server 2 through the communication unit 34 (STEP S21). The controller 31 also changes the displayed period of the second timeline screen 352 according to the operation, and causes the display 33 to display the changed second timeline screen 352 (STEP S22). STEP S22 may be performed in cooperation with the second server 2.

When receiving the operation information on the operation performed on the second timeline screen 352 from the display apparatus 3 through the communication unit 23, the controller 21 of the second server 2 determines whether the displayed period of the second timeline screen 352 is changed on the basis of the operation information. When determining that the displayed period is changed, the controller 21 obtains displayed period information of the second timeline screen 352 (STEP S23). The controller 21 then sends the obtained displayed period information to the display apparatus 3 through the communication unit 23 (STEP S24).

When receiving the displayed period information of the second timeline screen 352 from the second server 2 through the communication unit 34, the controller 31 of the display apparatus 3 generates, on the basis of the received displayed period information, the first timeline screen 353 that is changed to show the displayed period of the second timeline screen 352. The controller 31 then causes the display 33 to display the changed first timeline screen 353 (STEP S25). Then the second displayed period synchronization sequence ends.

For example, the controller 31 changes the displayed period of the first timeline screen 353 by: obtaining medical images of the display target patient that have been taken during the displayed period from the DB 121 of the server 1; generating the first timeline screen 353 on which the obtained medical images are arranged chronologically; and displaying the first timeline screen 353 on the display 33.

According to the second embodiment, displayed periods of multiple timeline screens being displayed on the display apparatus 3 can be made uniform. This can save time and effort of manipulating the individual timeline screens and changing their respective displayed periods to make these displayed periods uniform.

Further, the first and second displayed period synchronization sequences in the second embodiment can synchronize multiple timeline screens that include a Web timeline screen and a timeline screen displayed by an application program.

Further, according to the second embodiment, the displayed periods of timeline screens for multiple systems can be made uniform, so that information stored in the multiple systems can be viewed cross-sectionally.

Third Embodiment

Hereinafter, a third embodiment of the present invention is described.

The third embodiment exemplifies a case where the first and second timeline screens are displayed by programs (first application and second application) stored in the display apparatus 3.

[Configuration in Third Embodiment]

The configuration of the system in the third embodiment is the same as the display system 100 described in the first embodiment. The configurations of the first server 1, the second server 2, and the display apparatus 3, which consist the display system 100, are also the same as the configurations shown in FIG. 2 and FIG. 5.

In the third embodiment, the ROM of the controller 31 of the display apparatus 3 stores the first application for: reading out medical images of a patient specified with the operation unit 32 from the DB 121 of the first server 1; generating the first timeline screen 353 on which the medical images are arranged chronologically; causing the display 33 to display the first timeline screen 353; outputting operation information on operations performed on the first timeline screen 353 by a user; and changing the contents shown on the first timeline screen 353 according to the user's operations.

The ROM of the controller 31 also stores a program for: obtaining the operation information output by the first application; determining, on the basis of the obtained operation information, whether any operation to change the displayed period of the first timeline screen 353 is performed; when determining that an operation to change the displayed period is performed, obtaining displayed period information of the changed first timeline screen 353; causing the second application to change the displayed period of the second timeline screen 354 (see FIG. 4) to be the displayed period indicated by the obtained displayed period information and display the changed second timeline screen 354 on the display 33. Herein, the displayed period of the second timeline screen 354 is a period of timeline that is shown on the second timeline screen 354. The displayed period information of the second timeline screen 354 is information on the displayed period of the second timeline screen 354 (information indicating the displayed period). The displayed period information includes date information on at least the start and end dates of the displayed period.

The ROM of the controller 31 of the display apparatus 3 also stores the second application for: reading out examination result information of the patient specified with the operation unit 32 from the DB 221 of the second server 2; generating the second timeline screen 354 on which the examination result information is arranged chronologically; causing the display 33 to display the second timeline screen 354; outputting operation information on operations performed on the second timeline screen 354 by the user; and changing the contents shown on the second timeline screen 354 according to the user's operations.

The ROM of the controller 31 also stores a program for: obtaining the operation information output by the second application; determining, on the basis of the obtained operation information, whether any operation to change the displayed period of the second timeline screen 354 is performed; when determining that an operation to change the displayed period is performed, obtaining displayed period information of the changed second timeline screen 354; causing the first application to change the displayed period of the first timeline screen 353 to be the displayed period indicated by the obtained displayed period information and display the changed first timeline screen 353 on the display 33.

The ROM of the controller 31 of the display apparatus 3 also stores a program for performing a displayed period synchronization process, which is described below, in cooperation with the above-described programs and the first and second applications. The program is performed when the first timeline screen 353 and the second timeline screen 354 are both displayed on the display 33.

Further, the ROM of the controller 11 of the first server 1 stores a program for: reading out medical images requested by the display apparatus 3 from the DB 121; and sending the images to the display apparatus 3 through the communication unit 13.

Further, the ROM of the controller 21 of the second server 2 stores a program for: reading out examination result information requested by the display apparatus 3 from the DB 221; and sending the information to the display apparatus 3 through the communication unit 23.

[Operations of Third Embodiment]

Next, operations of the third embodiment are described.

Figure 9:
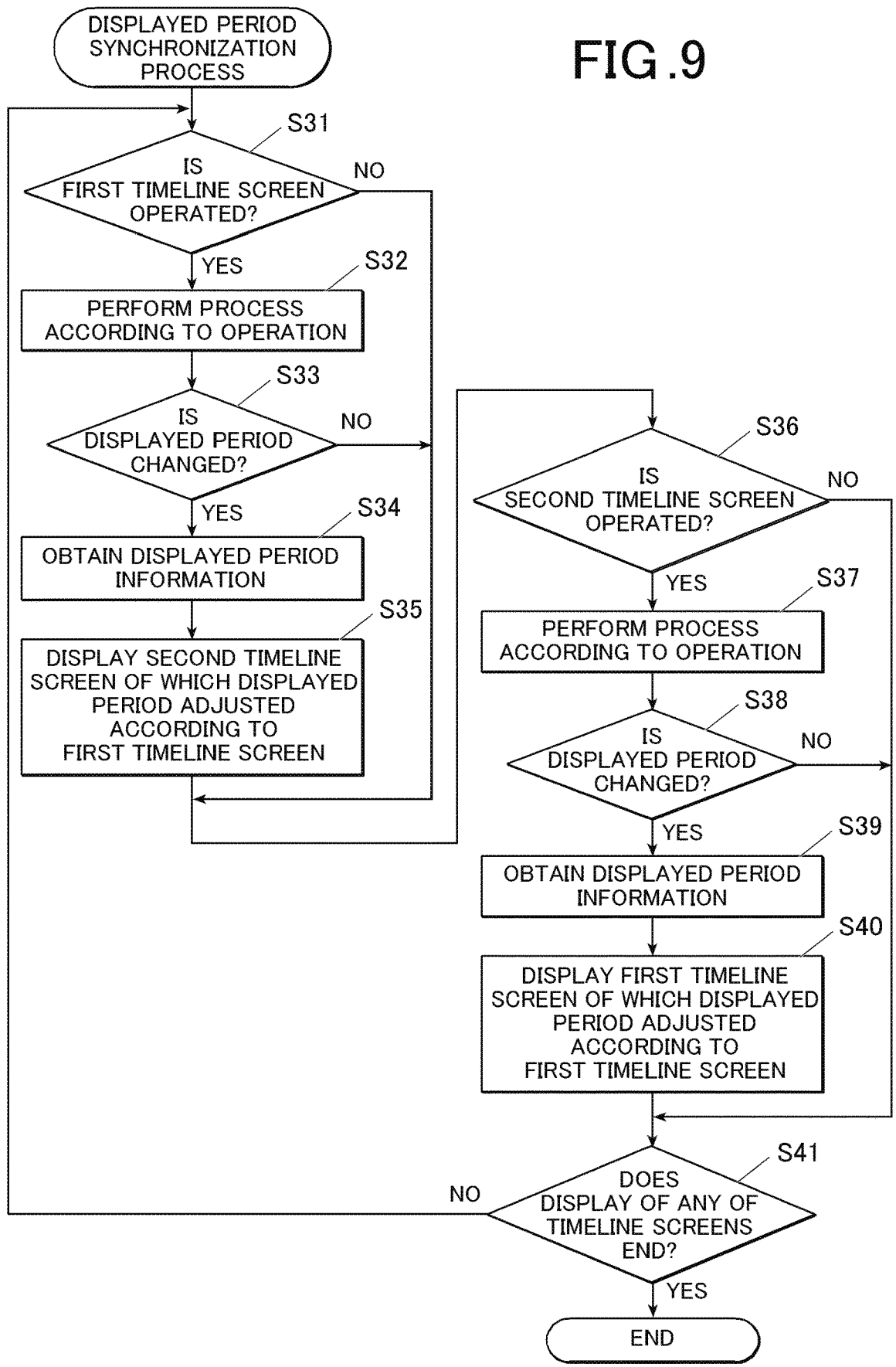
FIG. 9 is a flowchart showing procedure of a displayed period synchronization process performed by the display apparatus in a third embodiment.

FIG. 9 is a flowchart showing procedure of the displayed period synchronization process performed by the controller 31 of the display apparatus 3 in the third embodiment.

Herein, the display apparatus 3 is displaying the first timeline screen 353 and the second timeline screen 354 of a patient (display target patient).

The controller 31 of the display apparatus 3 determines whether an operation is performed on the first timeline screen 353 (STEP S31).

When determining that an operation is not performed on the first timeline screen 353 (STEP S31: NO), the controller 31 proceeds to STEP S36.

When determining that an operation is performed on the first timeline screen 353 (STEP S31: YES), the controller 31 performs a process corresponding to the operation performed on the first timeline screen 353 (STEP S32). For example, in response to an operation to change the displayed period being performed, the controller 31 obtains medical images of the display target patient from the DB 121 of the first server 1, generates the first timeline screen 353 on which the medical images are arranged chronologically, and causes the display 33 to display the generated first timeline screen 353.

Next, the controller 31 determines whether the displayed period of the first timeline screen 353 is changed (STEP S33).

When determining that the displayed period of the first timeline screen 353 is not changed (STEP S33: NO), the controller 31 proceeds to STEP S36.

When determining that the displayed period of the first timeline screen 353 is changed (STEP S33: YES), the controller 31 obtains the operation information and displayed period information of the first timeline screen 353 (STEP S34). On the basis of the obtained displayed period information, the controller 31 generates the second timeline screen 354 that is changed to show the first timeline screen 353 (the second timeline screen 354 showing examination result information of the displayed period indicated by the displayed period information) (STEP S35). The controller 31 then proceeds to STEP S36.

For example, the controller 31 obtains, from the DB 221 of the second server 2, the display target patient's examination result information during the displayed period, generates the second timeline screen 354 on which the examination result information is chronologically arranged, and displays the second timeline screen 354 on the display 33.

The controller 31 determines whether an operation is performed on the second timeline screen 354 (STEP S36).

When determining that an operation is not performed on the second timeline screen 354 (STEP S36: NO), the controller 31 proceeds to STEP S41.

When determining that an operation is performed on the second timeline screen 354 (STEP S36: YES), the controller 31 performs a process corresponding to the operation on the second timeline screen 354 (STEP S37). For example, when an operation to change the displayed period is performed, according to the operation, the controller 31 obtains examination result information of the display target patient from the DB 221 of the second server 2; generates the second timeline screen 354 on which the examination result information is arranged chronologically; and causes the display 33 to display the generated second timeline screen 354.

Next, the controller 31 determines whether the displayed period of the second timeline screen 354 is changed (STEP S38).

When determining that the displayed period of the second timeline screen 354 is not changed (STEP S38: NO), the controller 31 proceeds to STEP S41.

When determining that the displayed period of the second timeline screen 354 is changed (STEP S38: YES), the controller 31 obtains the operation information and displayed period information of the second timeline screen 354 (STEP S39). On the basis of the obtained displayed period information, the controller 31 generates the first timeline screen 353 that is changed to show the second timeline screen 354 (the first timeline screen 353 showing medical images of the displayed period indicated by the displayed period information) and causes the display 33 to display the changed first timeline screen 353 (STEP S40). The controller 31 then proceeds to STEP S41.

For example, the controller 31 obtains the display target patient's medical images during the displayed period from the DB 121 of the first server 1, generates the first timeline screen 353 on which the medical images are arranged chronologically, and causes the display 33 to display the generated first timeline screen 353.

The controller 31 determines whether an instruction to stop displaying any of the timeline screens is received (STEP S41).

When determining that an instruction to stop displaying any of the timeline screens is not received (STEP S41: NO), the controller 31 returns to STEP S31.

When determining that an instruction to stop displaying any of the timeline screens is received (STEP S41: YES), the controller 31 ends the displayed period synchronization process.

According to the third embodiment, the displayed periods of multiple timeline screens displayed on the display apparatus 3 can be made uniform. This can save time and effort of manipulating the individual timeline screens and changing their respective displayed periods to make these displayed periods uniform.

Further, the displayed period synchronization process in the third embodiment can synchronize multiple timeline screens that are displayed by different applications.

The third embodiment exemplifies a case where the display apparatus 3 is displaying two timeline screens. However, the number of timeline screens being displayed may be three or more. In a case where three or more timeline screens are displayed, the process from STEP S31 to STEP S35 (process from STEP S36 to STEP S40) may be performed for the respective timeline screens in turn. The displayed period synchronization process may end when the number of timeline screens being displayed becomes one or zero.

The first to third embodiments of the present invention described above are some of preferred examples of the display system and the display apparatus according to the present invention and not intended to limit the present invention.

For example, in the above embodiments, the timeline screens show different kinds of medical information of the same patient, such as medical images and examination result information, as display target information. However, this is not the limitation. The timeline screens may show medical information of different patients as the display target information. Further, the present invention may be applicable to displaying multiple timeline screens showing different kinds of information other than medical information, as the display target information. For example, the different kinds of information may be various kinds of record information consisting of documents and images.

Further, although the above embodiments exemplify cases where multiple timeline screens show medical information of the same medical facility, the multiple timeline screens may show information for different medical facilities. The present invention may be applicable to displaying timeline screens for different medical facilities of the same patient. This allows users to view medical information in multiple medical facilities of the same patient cross-sectionally without integrating the medical information.

Further, although the above embodiments exemplify cases where multiple timeline screens are made to show the same displayed period, the multiple timeline screens may be made to show information of the same display target patient. For example, in the first to third embodiments, the displayed period information may include patient information on display target patients. When one timeline screen changes its display target patient, the other timeline screen(s) may be made to show information of the same display target patient as the one timeline screen.

Further, as a computer-readable medium storing the programs of the present invention, a hard disk, a nonvolatile semiconductor memory, and the like are used in the above description. However, the computer-readable storage medium is not limited to these. As the computer-readable medium, a portable storage medium, such as a CD-ROM, may also be used. Also, as a medium that provides data of the programs of the present invention via a communication line, a carrier wave can be used.

The detailed configurations and detailed operations of the components consisting the display system 100 can also be appropriately modified without departing from the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A display system, comprising:
a display apparatus; and
a plurality of servers, each of the servers being configured to generate and control the display apparatus to display a respective one of plural timeline screens, the timeline screens showing different kinds of display target information in chronological order, and the display apparatus and the servers being communicably connected to each other,
wherein:
in response to a displayed period of a first timeline screen being changed, the displayed period being of a period of time indicated by the first timeline screen and having a start time and an end time later than the start time, and the first timeline screen being a timeline screen among the timeline screens that is generated and displayed on the display apparatus under control of a first server among the servers, the first server obtains information on the changed displayed period and sends the obtained information to a second server among the servers, the second server being different from the first server, and
in response to receiving the information on the changed displayed period from the first server, the second server controls a second timeline screen, which is a timeline screen among the timeline screens that is generated and displayed on the display apparatus under control of the second server, to show the display target information of the second timeline screen in the changed displayed period indicated by the received information.

2. The display system according to claim 1, wherein the first and second servers are Web servers, and the first and second timeline screens that are displayed on the display apparatus under control of the first and second servers are Web screens.

3. The display system according to claim 1, wherein the display target information is medical information on a same patient.

4. The display system according to claim 1, wherein each timeline screen of the plural timeline screens includes (i) a timeline indicating the displayed period of the timeline screen, and (ii) the display target information of the timeline screen, the display target information being displayed in association with the timeline such that each piece of display target information is displayed at a position corresponding to a timing within the displayed period at which the piece of display target information was acquired.

5. A display system, comprising:
a display apparatus; and
a plurality of servers, each of the servers being configured to generate and control the display apparatus to display a respective one of plural timeline screens, the timeline screens showing different kinds of display target information in chronological order, and the display apparatus and the servers being communicably connected to each other,
wherein:
in response to a displayed period of a first timeline screen being changed, the displayed period being of a period of time indicated by the first timeline screen and having a start time and an end time later than the start time, and the first timeline screen being a timeline screen among the timeline screens that is generated and displayed on the display apparatus under control of a first server among the servers, the first server obtains information on the changed displayed period and sends the obtained information to the display apparatus,
in response to receiving the information on the changed displayed period from the first server, the display apparatus sends the received information to a second server among the servers that corresponds to a second timeline screen among the timeline screens, the second server being different from the first server, and the second timeline screen being different from the first timeline screen, and
in response to receiving the information on the changed displayed period from the display apparatus, the second server controls the second timeline screen, which is generated and displayed on the display apparatus under control of the second server, to show the display target information of the second timeline screen in the changed displayed period indicated by the received information.

6. The display system according to claim 5, wherein the first and second servers are Web servers, and the first and second timeline screens that are displayed on the display apparatus under control of the first and second servers are Web screens.

7. The display system according to claim 5, wherein the display target information is medical information on a same patient.

8. A display system, comprising:
a display apparatus that generates and displays a first timeline screen showing first display target information in chronological order; and
a server that generates and causes the display apparatus to display a second timeline screen showing second display target information in chronological order, a kind of the second display target information being different from a kind of the first display target information, and the display apparatus and the server being communicably connected to each other,
wherein:
in response to a displayed period of the first timeline screen being changed, the displayed period being of a period of time indicated by the first timeline screen and having a start time and an end time later than the start time, the display apparatus obtains information on the changed displayed period and sends the obtained information to the server, and
in response to receiving the information on the changed displayed period from the display apparatus, the server generates the second timeline screen to show the second display target information in the changed displayed period indicated by the received information, and controls the display apparatus to display the generated second timeline screen.

9. The display system according to claim 8, wherein:
in response to a displayed period of the second timeline screen being changed, the server obtains information on the changed displayed period and sends the obtained information to the display apparatus, and
in response to receiving the information on the changed displayed period from the server, the display apparatus generates the first timeline screen to show the first display target information in the changed displayed period indicated by the received information, and displays the generated first timeline screen.

10. The display system according to claim 8, wherein the server is a Web server, and the second timeline screen is a Web screen.

11. The display system according to claim 8, wherein the first display target information and the second display target information are medical information on a same patient.

* * * * *